US009687242B2

(12) United States Patent
Hendriksen et al.

(10) Patent No.: US 9,687,242 B2
(45) Date of Patent: Jun. 27, 2017

(54) OCCLUSION DEVICE (75) Inventors: Per Hendriksen, Herlufmagle (DK);
Jacob Lund Clausen, Kgs. Lyngby
(DK); Frank K. Christiansen, Haslev
(DK)

(73) Assignee: **COOK MEDICAL TECHNOLOGIES
LLC**, Bloomington, IN (US)

( * ) Notice: Subject to any disclaimer, the term of this
patent is extended or adjusted under 35
U.S.C. 154(b) by 211 days.

(21) Appl. No.: 12/936,110

(22) PCT Filed: Apr. 3, 2009

(86) PCT No.: PCT/US2009/039454
§ 371 (c)(1),
(2), (4) Date: Nov. 8, 2010

(87) PCT Pub. No.: WO2009/124247
PCT Pub. Date: Oct. 8, 2009

(65) Prior Publication Data
US 2011/0054512 A1 Mar. 3, 2011

Related U.S. Application Data (60) Provisional application No. 61/072,944, filed on Apr. 3, 2008.

(51) Int. Cl.
*A61M 29/00* (2006.01)
*A61B 17/12* (2006.01)

(52) U.S. Cl.
CPC .... *A61B 17/12022* (2013.01); *A61B 17/1204*
(2013.01); *A61B 17/1219* (2013.01);
(Continued)

(58) Field of Classification Search
CPC .......... A61B 17/12022; A61B 17/1204; A61B
17/12109; A61B 17/12177;
(Continued)

(56) References Cited

U.S. PATENT DOCUMENTS 4,085,757 A * 4/1978 Pevsner ........... A61B 17/12031
604/907
5,181,921 A * 1/1993 Makita ............. A61B 17/12109
604/247
(Continued)

FOREIGN PATENT DOCUMENTS

WO    WO 01/49213    7/2001
WO    WO 2004/010845   2/2004
(Continued)

*Primary Examiner* — Amy R Weisberg
(74) *Attorney, Agent, or Firm* — Brinks Gilson & Lione (57) ABSTRACT An occlusion device (30) includes at least one self-expanding frame (42, 44) and graft material (46). Occlusion occurs by constricting the graft material (46) at a substantially central point or at an end of the device. The constriction is sized such that a guide wire (34) is able to pass therethrough. A valve mechanism (50) includes a screen (52) made from a resilient material and which includes a closable opening (54). The valve mechanism (50) allows a guide wire to pass through the occlusion device (30) while an effective physical barrier is maintained after removal of the guide wire (34).

8 Claims, 6 Drawing Sheets (52) U.S. Cl.
CPC .. *A61B 17/12109* (2013.01); *A61B 17/12172* (2013.01); *A61B 17/12177* (2013.01); *A61B 2017/1205* (2013.01)

(58) Field of Classification Search
CPC .......... A61B 17/1219; A61B 17/12027; A61B 17/12031; A61B 17/12036; A61B 17/12045; A61B 17/12172; A61B 2017/1205
USPC ....... 606/200; 623/1.13, 1.23–1.26, 1.3–1.31
See application file for complete search history.

(56) References Cited

U.S. PATENT DOCUMENTS

| | | | | |
|---|---|---|---|---|
| 5,382,261 | A * | 1/1995 | Palmaz | A61B 17/12022 604/907 |
| 5,499,995 | A * | 3/1996 | Teirstein | A61B 17/12022 606/192 |
| 5,683,411 | A * | 11/1997 | Kavteladze | A61B 17/0057 606/200 |
| 5,800,525 | A * | 9/1998 | Bachinski | A61F 2/01 606/200 |
| 5,957,949 | A * | 9/1999 | Leonhardt | A61F 2/07 606/108 |
| 6,193,748 | B1 * | 2/2001 | Thompson | A61B 17/12022 623/1.3 |
| 6,254,633 | B1 * | 7/2001 | Pinchuk | A61B 17/12022 606/200 |
| 6,458,138 | B1 * | 10/2002 | Sydney | A61F 2/958 604/265 |
| 6,458,153 | B1 * | 10/2002 | Bailey | A61F 2/2418 623/1.24 |
| 6,544,291 | B2 * | 4/2003 | Taylor | A61F 2/0004 623/1.25 |
| 6,712,836 | B1 * | 3/2004 | Berg | A61B 17/0057 606/213 |
| 7,118,600 | B2 * | 10/2006 | Dua | A61F 2/04 623/23.64 |
| 7,192,442 | B2 * | 3/2007 | Solem | A61F 2/2451 606/191 |
| 7,798,147 | B2 * | 9/2010 | Hendricksen | A61B 17/12022 128/200.24 |
| 8,038,708 | B2 * | 10/2011 | Case | A61F 2/2412 623/1.24 |
| 8,251,067 | B2 * | 8/2012 | Hendricksen | A61B 17/12022 128/200.26 |
| 8,764,772 | B2 * | 7/2014 | Tekulve | A61B 17/08 606/151 |
| 8,870,944 | B2 * | 10/2014 | Sochman | A61F 2/2418 623/1.24 |
| 9,364,354 | B2 * | 6/2016 | Ben-Muvhar | A61F 2/91 |
| 2002/0082638 | A1 * | 6/2002 | Porter | A61B 17/12113 606/195 |
| 2002/0138135 | A1 * | 9/2002 | Duerig | A61F 2/2418 623/1.24 |
| 2003/0097172 | A1 * | 5/2003 | Shalev | A61F 2/88 623/1.31 |
| 2003/0187474 | A1 * | 10/2003 | Keegan | A61F 2/0095 606/200 |
| 2003/0212429 | A1 * | 11/2003 | Keegan | A61F 2/01 606/200 |
| 2003/0220667 | A1 * | 11/2003 | van der Burg | A61B 17/0057 606/200 |
| 2003/0229366 | A1 * | 12/2003 | Reggie | A61B 1/3137 606/158 |
| 2004/0034366 | A1 * | 2/2004 | van der Burg | A61B 17/0057 606/119 |
| 2004/0055606 | A1 * | 3/2004 | Hendricksen | A61B 17/12022 128/207.14 |
| 2004/0210194 | A1 * | 10/2004 | Bonnette | A61B 17/22 604/167.06 |
| 2004/0236412 | A1 * | 11/2004 | Brar | A61B 17/12045 623/1.31 |
| 2004/0243073 | A1 * | 12/2004 | Lockwood | A61M 1/0084 604/313 |
| 2005/0055082 | A1 * | 3/2005 | Ben Muvhar | A61F 2/91 623/1.15 |
| 2005/0119684 | A1 * | 6/2005 | Guterman | A61B 17/12022 606/198 |
| 2005/0171556 | A1 * | 8/2005 | Murphy | A61B 17/12022 606/108 |
| 2005/0182481 | A1 * | 8/2005 | Schlick | A61F 2/07 623/1.15 |
| 2005/0182483 | A1 * | 8/2005 | Osborne | A61F 2/2403 623/1.24 |
| 2005/0203568 | A1 * | 9/2005 | Burg et al. | 606/200 |
| 2006/0030920 | A1 * | 2/2006 | Ben-Muvhar | A61F 2/958 623/1.3 |
| 2006/0058820 | A1 * | 3/2006 | Mialhe | A61B 17/0057 606/157 |
| 2006/0106449 | A1 * | 5/2006 | Ben Muvhar | A61B 17/12022 623/1.15 |
| 2006/0106450 | A1 * | 5/2006 | Ben Muvhar | A61B 17/12022 623/1.15 |
| 2006/0135947 | A1 * | 6/2006 | Soltesz | A61B 17/12104 604/516 |
| 2006/0265054 | A1 * | 11/2006 | Greenhalgh | A61F 2/07 623/1.31 |
| 2006/0287668 | A1 * | 12/2006 | Fawzi | A61F 2/013 606/200 |
| 2007/0162103 | A1 * | 7/2007 | Case | A61F 2/2412 623/1.13 |
| 2008/0262518 | A1 * | 10/2008 | Freudenthal | A61B 17/0057 606/151 |
| 2009/0192601 | A1 * | 7/2009 | Rafiee | A61F 2/2436 623/2.11 |
| 2010/0049306 | A1 * | 2/2010 | House | A61F 2/2418 623/1.26 |
| 2010/0174366 | A1 * | 7/2010 | Avior | A61F 11/002 623/10 |
| 2010/0249923 | A1 * | 9/2010 | Alkhatib | A61F 2/2418 623/2.18 |
| 2010/0312268 | A1 * | 12/2010 | Belson | A61F 2/01 606/200 |
| 2011/0106234 | A1 * | 5/2011 | Grandt | A61F 2/86 623/1.11 |
| 2011/0238168 | A1 * | 9/2011 | Pellegrini | A61F 2/2412 623/2.17 |
| 2012/0083832 | A1 * | 4/2012 | Delaloye | A61B 17/0057 606/213 |
| 2012/0221100 | A1 * | 8/2012 | Huber | A61B 17/22004 623/2.17 |
| 2013/0030521 | A1 * | 1/2013 | Nitzan | A61B 17/0057 623/2.13 |
| 2013/0053879 | A1 * | 2/2013 | Gailloud | A61B 17/12022 606/191 |
| 2014/0031928 | A1 * | 1/2014 | Murphy | A61B 17/0057 623/2.18 |
| 2014/0128659 | A1 * | 5/2014 | Heuring | A61M 1/101 600/16 |
| 2014/0135908 | A1 * | 5/2014 | Glozman | A61F 2/2418 623/2.11 |
| 2014/0350565 | A1 * | 11/2014 | Yacoby | A61F 2/2436 606/108 |
| 2015/0039017 | A1 * | 2/2015 | Cragg | A61B 17/12172 606/200 |
| 2016/0030052 | A1 * | 2/2016 | Cragg | A61B 17/12172 606/200 |
| 2016/0120646 | A1 * | 5/2016 | Dwork | A61F 2/2469 623/2.18 |

FOREIGN PATENT DOCUMENTS

| | | |
|---|---|---|
| WO | WO 2004/058097 | 7/2004 |
| WO | WO 2009/124247 | 10/2009 |

* cited by examiner

OCCLUSION DEVICE

CROSS REFERENCE TO RELATED APPLICATIONS

This application claims the benefit of priority to PCT/US2009/039454 filed Apr. 3, 2009 which claims the benefit of Provisional Patent Application Ser. No. 61/072,944 filed Apr. 3, 2008, the entire contents of which are hereby incorporated herein by reference.

TECHNICAL FIELD

The present invention relates to an occlusion device.

BACKGROUND

Aneurysms present a potentially life-threatening problem. An aneurysm is the result of a weak area in a vessel wall, resulting in bulging in the weak area at a particular site in the vessel wall. Untreated aneurysms stand the risk of rupturing, which can result in a stroke or even death. It has become an accepted form of treatment for aneurysms, or for other medical situations where prevention of blood flow to the site of the defect is desired, to occlude the vessel by means of a device implanted into the vessel in question.

Devices for occluding body vessels are known. Occlusion devices that are intended to block blood vessels generally rely on the clotting of blood to provide occlusion. Such devices may include features that promote blood clotting. Nevertheless, it generally takes a variable amount of time for sufficient clotting to have occurred to provide full blockage of a blood vessel. The time taken depends on many factors such as vessel size and pressure and presence or absence of anti-coagulants. It is thus difficult to predict, for any particular patient, by when proper occlusion will have occurred. When such devices are used, a surgeon may not be sure before a patient is discharged from hospital that effective occlusion will occur.

Some prior art occlusion devices take advantage of provision of a physical barrier in a vessel to be occluded. These may take the form of a balloon, or graft material attached to a frame, for example. In such devices, however, the physical barrier is generally not well anchored within a vessel, and is subject to displacement after implantation.

SUMMARY

The present invention seeks to provide an improved occlusion device.

According to a first aspect of the present invention, there is provided an occlusion device including: a frame having a longitudinal axis for anchoring the device against an internal wall of a vessel to be occluded, wherein the frame includes a portion for contacting the internal wall of a vessel to be occluded, the wall contacting portion extending along at least part of its longitudinal axis; at least one occlusion membrane attached to the frame, the occlusion membrane having a portion for contacting the internal wall of a vessel to be occluded, wherein the occlusion membrane is attached to the frame at least at its wall-contacting portion, the attachment extending substantially entirely around the frame; wherein the act of expanding the device within the vessel causes the occlusion membrane to form a physical barrier within a vessel to be occluded.

Attachment of an occlusion membrane to a frame allows controlled expansion and positioning of the membrane. The frame acts to anchor the membrane against an internal wall of a vessel to be occluded thus holding the occlusion membrane in place. This assists in providing immediate occlusion of a vessel without the need for blood clotting. As the frame has a wall-contacting portion that extends along at least a portion of its longitudinal axis, the anchoring point within a vessel is spread around and along the vessel wall minimising damage to the vessel wall.

Preferably, the device includes a guide wire receiving element. This enables the device to be deployed over a guide wire, which greatly facilitates deployment of the device.

The guide wire receiving element may be a closable opening. The opening allows a guide wire to pass therethrough, and closes upon removal of a guide wire. This arrangement not only enables the device to be deployed using a guide wire, but ensures that effective occlusion is maintained after removal of the guide wire.

In an embodiment, the closable opening is formed in an occlusion barrier extending across a lumen of the device. The occlusion barrier thus prevents blood flow through the lumen of the device.

The occlusion barrier may extend across a constricted portion of the device. Occlusion may thus be achieved partially by the occlusion membrane, and partially by the occlusion barrier.

In the preferred embodiment, the occlusion membrane is not fabricated from a bioabsorbable material. The occlusion device therefore does not require blood clotting and thus does not rely on blood clotting for long-term occlusion.

In another embodiment, the device includes a tubular frame; a first conical frame provided at a distal end of the tubular frame, the apex of the cone pointing in the distal direction; a second conical frame provided at a proximal end of the tubular frame, the apex of the cone pointing in the proximal direction; wherein at least the first conical frame and the second conical frame are provided with overlying graft material.

In an embodiment, the device includes at least one frame; at least one valve, the valve having a diameter less than the diameter of a vessel to be occluded; graft material (an occlusion membrane) extending from the frame to the valve; and the valve including a transverse occlusion barrier, the occlusion barrier including a closable opening for a guide wire.

The device may include a first frame and a second frame, the first frame provided at a proximal end of the device and the second frame provided at a distal end of the device; wherein the valve is arranged substantially centrally between the first and second frames, and wherein the graft material extends from the first frame to the valve and from the second frame to the valve.

According to a second aspect of the present invention, there is provided a kit including an occlusion device as described above and a deployment device.

Further aspects, features, and advantages of the invention will become apparent from consideration of the following description and the appended claims when taken in connection with the accompanying drawings.

BRIEF DESCRIPTION OF THE DRAWINGS

Preferred embodiments of the present invention are described below, by way of example only with reference to the accompanying drawings in which.

DETAILED DESCRIPTION

It is to be understood that the Figures are schematic and do not show the various components to their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a frame or an occlusion device, the term proximal refers to a location that in use is closest to the patient's heart, in the case of a vascular implant, and the term distal refers to a location furthest from the patient's heart.

Figure 1:
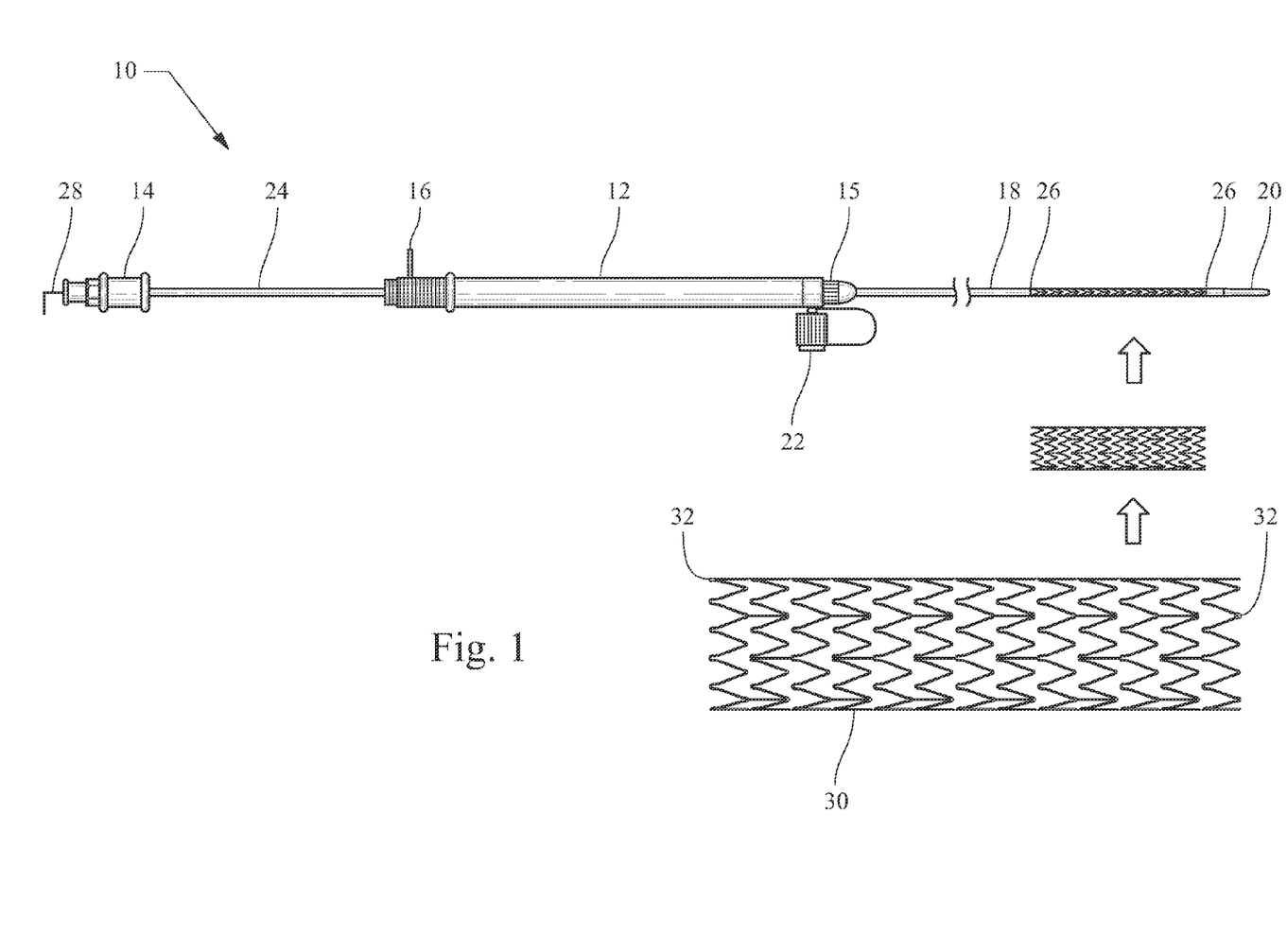
FIG. 1 is a side elevational view of an example of an implant delivery device in accordance with one embodiment of the present invention.
Figure 2:
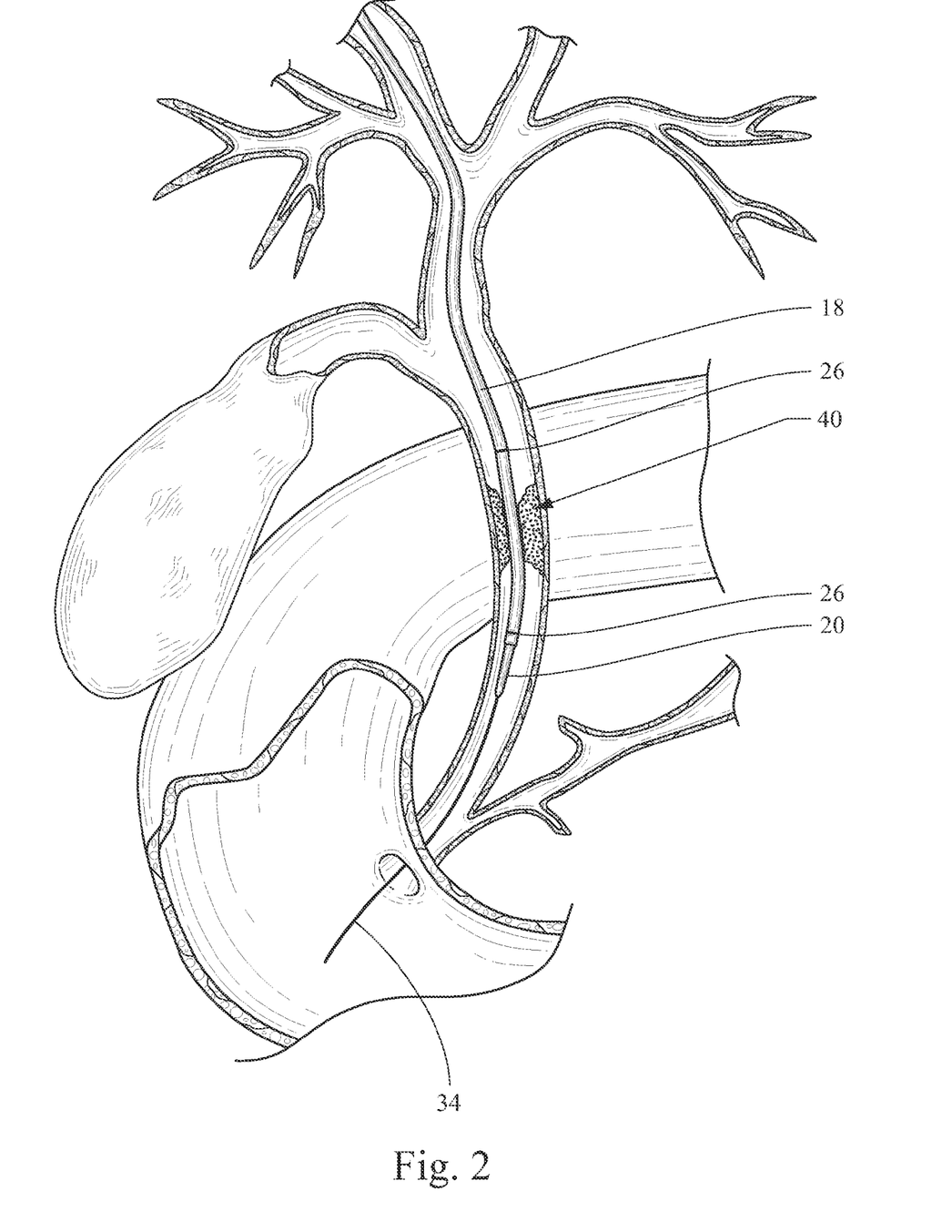
FIGS. 2 and 3 are side views of the implant delivery device of FIG. 1 during deployment of an implant.
Figure 3:
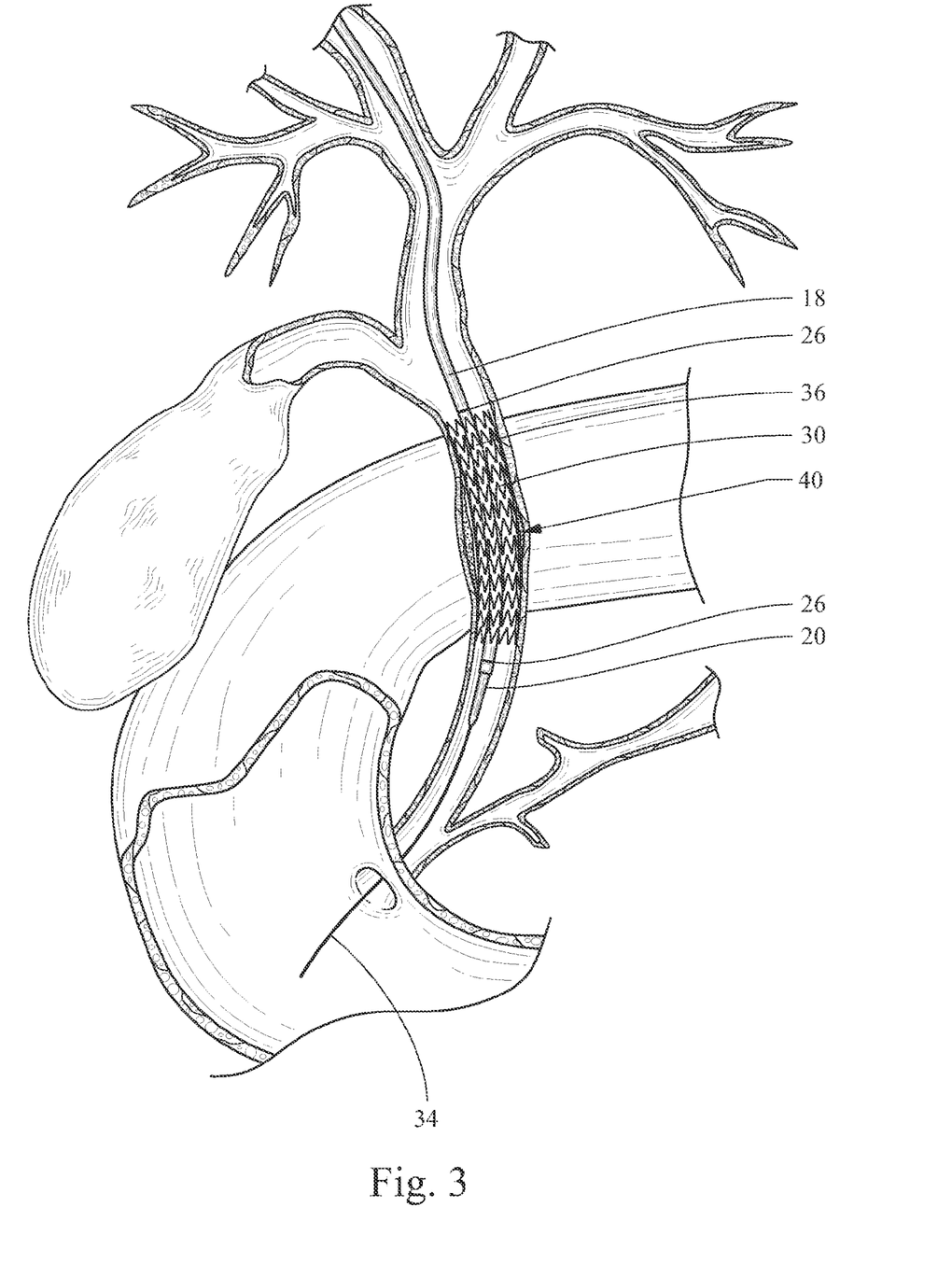

An example of a delivery system is shown in FIGS. 1 to 3. This description is given by way of background.

The delivery assembly 10 shown in FIG. 1 includes a tubular handle 12, preferably made of a plastics material, and a hub 14, also made of a plastics material. A safety lock 16 is removably fitted into a portion of the handle 12, for purposes to be described below.

An introducer catheter (or sheath) 18, made of any of the conventional or otherwise suitable catheter materials known in the art, extends from and is attached to the handle 12, in this example by a threaded nut 15. Housed within the introducer catheter 18 is an inner catheter 36 (visible in FIG. 3) which carries an implant 30 and which is provided at its distal end with a flexible introducer tip 20. The inner catheter 36 has a bore passing therethrough for the introduction of a guide wire 34, shown in FIGS. 2 and 3.

The handle 12 is provided with a side arm flushing port 22, of conventional form, for flushing the space inside the introducer catheter 18.

The hub 14 is fixed to a metal cannula 24 which is itself attached to the inner catheter 36.

The delivery assembly 10 is provided with radiopaque markers 26. In this example, the proximal marker 26 is located on the introducer catheter 18, while the distal marker 26 is provided on the inner catheter 36, as will be apparent from FIG. 3.

The hub 14 is provided with an inner support stylet 28 operable to receive and support a guide wire 34, which guide wire 34 passes through the inner stylet 28, the hub 14, the metal cannula 24, the inner catheter 26 and out of distal end of the introducer tip 20.

The distal end of the inner catheter 36, adjacent the introducer tip 20, supports an implant 30. The introducer catheter 18 overlies and acts as a holding sheath for the implant 30. The implant 30 is provided, in this example, with its own radiopaque markers 32, in a form known in the art.

The safety lock 16 acts to lock the metal cannula 24 in an extended position relative to the handle 12, as shown in FIG. 1, and thus to lock the introducer catheter 18 over the inner catheter 36, until the time of deployment.

Referring now to FIGS. 2 and 3, an implant 30 is deployed in a vessel, in this case in the biliary tract, of a patient, by first introducing a guide wire 34 through an access catheter (not shown) across the distal segment of the target lesion 40 of the vessel. Once the guide wire 34 is in place, the introducer catheter 18 is fed over the guide wire 34 until the distal end of the introducer catheter 18 is over the target lesion 40. During this process the introducer catheter 18 is flushed with saline solution through the side arm flushing port 22.

Once the introducer catheter 18 has been located at the deployment site, the implant 30 held by the delivery assembly 10 is ready to be deployed. This position of the delivery assembly 10 is shown in FIG. 2, with the two markers 26 appearing either side of the target lesion site 40.

In order to deploy the implant 30, the safety lock 16 is removed, which allows the handle 12 to be slid over the metal cannula 24. In other words, once the safety lock 16 has been removed, the handle 12 can be pulled back whilst holding the hub 14 steady. This action of pulling back the handle 12 retracts the introducer catheter 18 from the inner catheter 36 with the result that the implant 30 is exposed and allowed to expand gradually as the introducer catheter 18 moves backwards relative to the inner catheter 36. FIG. 3 shows the introducer catheter 18 fully withdrawn and the implant 30 fully deployed at the target lesion 40.

Once the implant 30 has been deployed, the delivery assembly 10 can be withdrawn by pulling the handle 12 and the hub 14 together in a withdrawal direction, that is, out of the patient.

Figure 4:
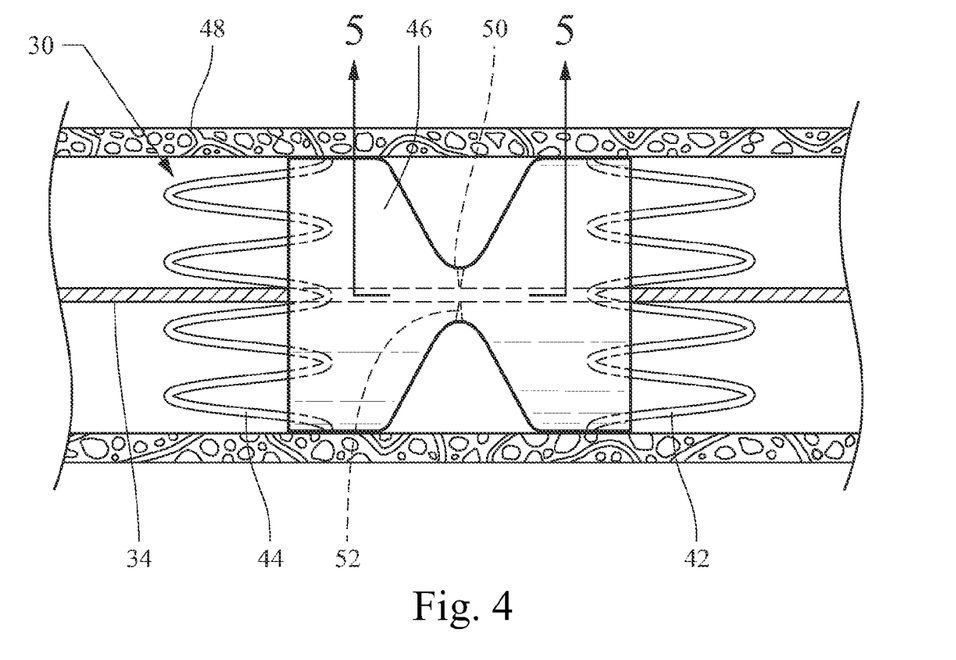
FIG. 4 is a side view of an occlusion device in accordance with one embodiment of the present invention.

Turning now to FIG. 4, an embodiment of an occlusion device 30 is shown. The occlusion device 30 includes first and second frames 42, 44, which in this embodiment are self-expanding. The first self-expanding frame 42 is located at the proximal end of the occlusion device 30, and the second self-expanding frame 44 is located at the distal end of the occlusion device 30. Attached to and surrounding each frame 42, 44 is a generally tubular piece of graft material (or occlusion membrane) 46. In this embodiment, the graft material or occlusion membrane 46 is preferably attached to the outside of each self-expanding frame 42, 44 and radially surrounds at least a portion of each self-expanding frame 42, 44. The graft material or occlusion membrane 46 may be attached to the self-expanding frames by stitching or indwelling, for example. The graft material or occlusion membrane 46 thus assists in forming a seal between each self-expanding frame 42, 44 and the wall 48 of a vessel into which the occlusion device 30 has been placed.

In this embodiment, the occlusion device 30 includes a constriction substantially centrally along the length of the device 30. This is formed by a valve 50 located within the occlusion device 30. The valve 50 is described in more detail below. The diameter of the valve 50 is substantially less than the diameter of the vessel in which the occlusion device 30 is to be placed. Its diameter is preferably substantially the same as that of the self-expanding frames 42, 44 prior to expansion. At the location of the valve 50, the graft material 46 is gathered towards the central longitudinal axis of the occlusion device 30 and attached to the valve 50.

Figure 5:
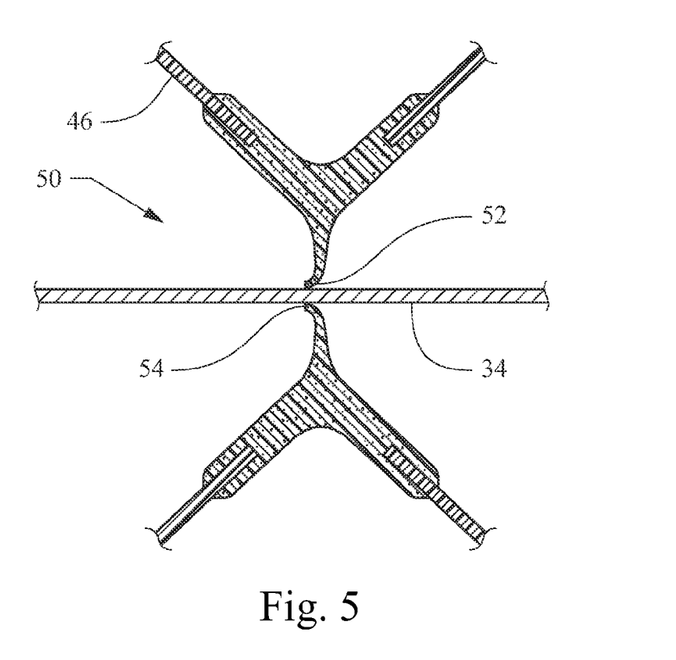
FIG. 5 is an elongated view of the circle in FIG. 4.

FIG. 5 shows the valve 50 in more detail. The valve 50 includes an occlusion barrier 52. The occlusion barrier 52 includes an opening 54, which may be a pin-prick or provided by overlapping leaves. The occlusion barrier 52 is made from a resilient material such as silicone, polyurethane, expanded PTFE, a plastic material or even graft material so that the opening 54 is closable and is biased into its closed configuration. It is not necessary to use a rubberised material.

Attachment of the graft material 46 to the valve 50 at a substantially central point, thus gives the occlusion device 30 an overall shape resembling an hourglass in this embodiment.

In use, the occlusion device 30 can be deployed in a vessel by means of a delivery assembly such as that described in relation to FIGS. 1 to 3. After the occlusion device 30 has been allowed to expand, the guide wire 34 can be withdrawn. Once the guide wire 34 has been withdrawn, the opening 54 closes due to the resilient nature of the occlusion barrier 52. The occlusion device 30 thus provides a physical barrier across the lumen of a vessel by means of the graft material 46 that contacts the vessel wall 48 and extends radially inwardly at the point of the constriction. Occlusion is completed by presence of the occlusion barrier 52.

There are several advantages to the above-described embodiment. The graft material 46 being pulled to the constriction, along with the occlusion barrier 52 provide a physical barrier extending across the entire diameter of a vessel. This means that upon expansion of the occlusion device 30, immediate occlusion of the vessel is obtained. It is not necessary to wait for blood clotting to occur to achieve blocking of the vessel nor is it necessary to manipulate the device further to achieve occlusion. Furthermore, since blood clotting is not required for occlusion, the device 30 can be used to block other types of vessel.

The opening 54 enables the occlusion device 30 to be used over a guide wire 34. This aids in location and positioning of the occlusion device 30. Because the opening 54 is closable (the occlusion barrier 52 being made of a resilient material), when the guide wire is removed, the integrity of the barrier is maintained.

Attachment of the graft material 56 to self-expanding frames 42, 44 provides secure anchoring to the vessel wall 48. Furthermore, having the graft material 46 extend at least partially over the self-expanding frames 42, 44 assists in forming a secure seal between the graft material 46 and the vessel wall 48.

The self-expanding frames 42, 44 provide a relatively large contact area between the occlusion device 30 and the vessel wall 48. This provides secure positioning of the occlusion device 30 within the vessel and reduces the chance of the pressure of blood flow dislodging the device 30. Furthermore, the risk of damage to the vessel wall 48 is reduced compared to devices with localized contact between the occlusion device 50 and the vessel wall 48. This is because the self-expanding frames 42, 44 spread the load around the vessel wall 48.

The hourglass shape of the occlusion device 30 enables a single occlusion device 30 to be suitable for vessels of varying different sizes. The arrangement can be such that expansion of the self-expanding frame 42, 44 is limited only by the size of the vessel not by the size of the graft material 46. The bi-directionality of the occlusion device 30 aids in the deployment process. During deployment, if it is found that the occlusion device 30 is not correctly positioned, the occlusion device 30 can be withdrawn back into introducer catheter 18, repositioned, and then redeployed. Furthermore, the positioning of the device 30 is not dependent upon the direction of blood flow within the vessel.

There are many modifications that could be made to the above-described embodiment. Other ways of achieving the valve function may be envisaged. For example, the occlusion barrier 52 may be formed from two overlapping flaps or leaves of material. In another modification the occlusion barrier 52 may resemble a blood vessel valve, though arranged not to allow normal blood flow therethrough. A self-healing plastic could be used to form occlusion barrier 52. For small blood vessels a valve may not be required at all. A valve also may not be required if modifications are made to allow the guide wire to run alongside the device rather than through the device.

In a modification of the occlusion device 30 illustrated in FIG. 4, the portion of the graft material 46 that overlies the self-expanding frames 42, 44 could be thinner than that extending from the frames 42, 44 to the valve 50. In this way a good seal between the frames 42, 44 and the vessel wall 48 may be obtained whilst reducing increase in diameter of the unexpanded frame due to the overlying graft material 46.

The graft material need not overlie the frame; the graft material may be attached to the frame internally. Also, the graft material could be supported by frames or struts extending from the vessel wall-contacting frames to the constriction.

Figure 6:
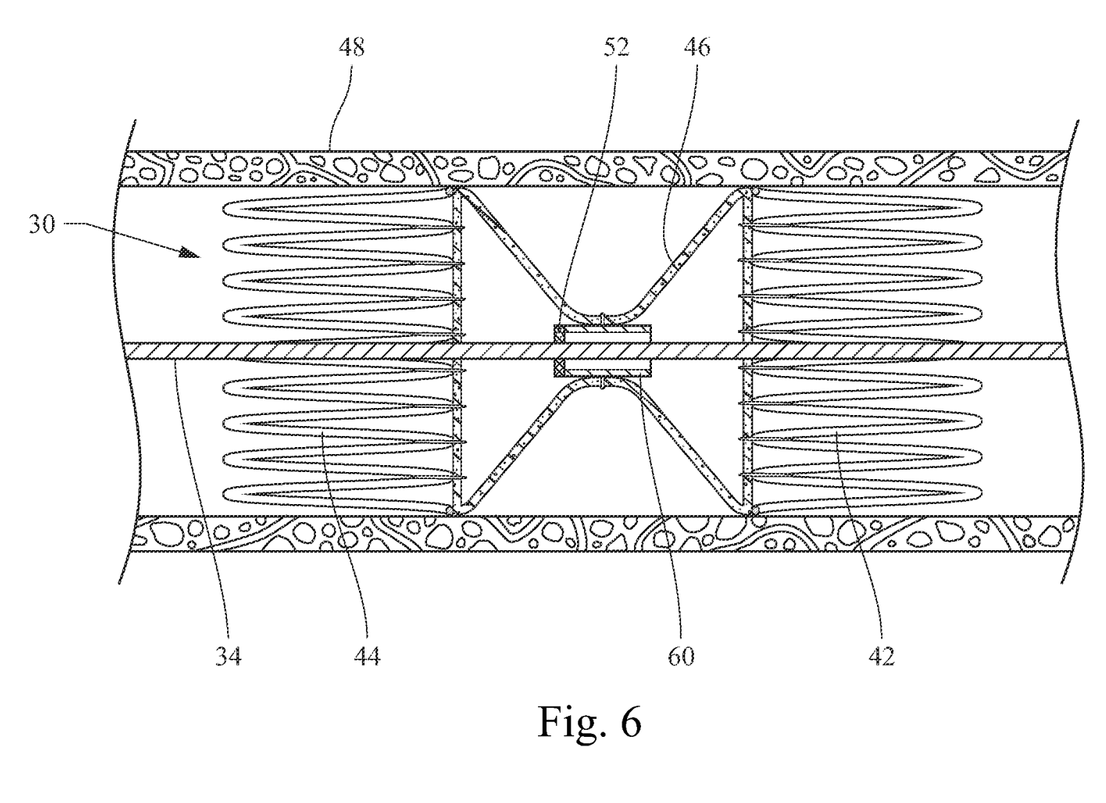
FIG. 6 is a side view of an occlusion device in accordance with another embodiment of the present invention.

Of course, other modifications are possible. The graft material 46 may be supported by an underlying structure, for example, a mesh-like structure formed from the same material as the self-expanding frames 42, 44. In the embodiments of FIGS. 4 and 6, this may extend from the first and second self-expanding frames 42, 44 to the constriction.

In other embodiments the valve 50 (and thus the constriction) may be located at an end of the occlusion device 30. This results in an occlusion device being substantially frusto-conical in shape or resembling the shape of half an hourglass. In such embodiments, the valve 50 would preferably be located at the distal end of the occlusion device 30.

Although the above-described embodiment uses self-expanding frames, the skilled person will appreciate that balloon-expandable frames could also be used.

The device could be used to provide temporary occlusion or permanent occlusion.

The frames could include barbs to assist in attachment of the device to a vessel wall. An advantage of including barbs that engage the vessel wall is that the barbs not only assist in fixing the device in place, but also irritate the vessel wall. This promotes restenosis, which in turn assists in providing improved fixation of the device within the blood vessel, and improved occlusion.

FIG. 6 illustrates an occlusion device 30 with some modifications. These modifications are not inter-dependent and may independently be applied to the embodiment of FIG. 4.

In the occlusion device 30 shown in FIG. 6, the graft material 46 is attached to the distal end of the first self-expanding frame 42 and to the proximal end of the second self-expanding frame 44. This arrangement has the advantage of allowing the occlusion device 30 to be compressed to a greater extent prior to deployment. This is because the graft material 46 does not take up space between the self-expanding frames 42, 44 and the introducer catheter 18.

In the occlusion device 30 shown in FIG. 6, the constriction is formed by a tube 60. The tube is sized so as to allow a guide wire 34 to pass therethrough, and the constriction is formed by the graft material 46 being attached to the outer surface of the tube 60. The attachment could be made by a suitable adhesive or by an overlying ring for example. The tube 60 is provided with a occlusion barrier 52 extending transversely across its lumen so as to complete the barrier. As in the occlusion device 30 shown in FIG. 4, the occlusion barrier 52 includes a closable opening 54 for passage of the guide wire 34.

Figure 7:
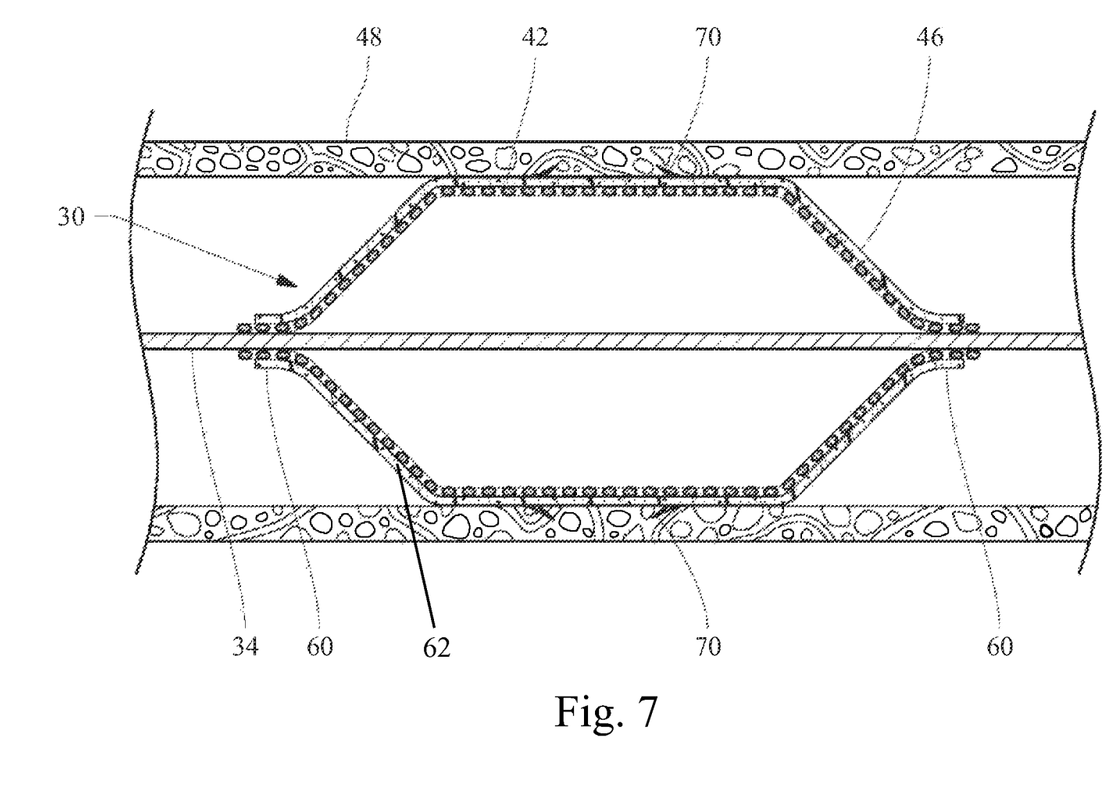
FIG. 7 is a side view of an occlusion device in accordance with another embodiment.

FIG. 7 illustrates another embodiment of an occlusion device. This embodiment has two conical members: a first conical member provided at the distal end of the tubular member 62, the apex of the conical member pointing in the distal direction, and a second conical member provided at the proximal end of the tubular member 62, the apex of the conical member pointing in the proximal direction. In this version, two conical portions of graft material 46 are provided, one at each end of the device. In this embodiment, the graft material 46 preferably overlies a frame, and partially extends along the vessel wall-contacting part of the occlusion device to provide improved sealing.

The frame 42 is preferably formed from a metal tube having longitudinal cuts therein to form longitudinally extending struts. The struts can then be expanded radially outwardly at a central portion of the structure to form an open basket-like rounded structure and so that the device can engage with a vessel wall. The very proximal and distal ends of the tube are not slit, and thus form the apices of the cones and preferably tubular end pieces. These are constrictions 60 that enable the graft material 46 to provide occlusion by extending across the vessel from the non-expanded tubes or end-pieces 60 to the expanded portion of the device 30. Depending upon the size of the vessel, the unexpanded tubes or end-pieces 60 may include a valve similar to that shown in FIG. 5.

The frame 42 may be coated with hydrogel. This expands when it comes into contact with a liquid (such as blood) and assists in providing improved sealing.

Laser cutting can also be used to form one or more barbs 70 in the expandable portion of the device 30. These extend outwardly to engage with the vessel wall. As described above, these can irritate the vessel wall in order to cause restenosis.

Many modifications could be made to the embodiment of FIG. 7. The modifications described above with reference to the embodiment of FIG. 4 and FIG. 6 may be applied to the embodiment of FIG. 7 as appropriate.

The frame 42 need not be formed from laser cut tubing. It could be braided or knitted for example. A coating could be applied by spraying or electrospinning. Other examples of coatings that may be applied to the frame 42 include polyurethane, expanded PTFE, Thoralon, and non-porous silicone.

The graft material 46 may be hydrophobic.

While the present invention has been described in terms of preferred embodiments, it will be understood, of course, that the invention is not limited thereto since modifications may be made to those skilled in the art, particularly in light of the foregoing teachings.

The invention claimed is:

1. An occlusion device for occluding a vessel having an internal wall, the occlusion device comprising:
a frame consisting of a proximal frame and a distal frame for anchoring the device against the internal wall of the vessel to be occluded, the proximal frame being disposed at a proximal end of the occlusion device, the distal frame being at a distal end of the occlusion device, the device having a longitudinal axis therethrough, the proximal frame being longitudinally spaced apart from the distal frame, each of the proximal frame and the distal frame having a tubular metal construction comprising a plurality of struts, each of the proximal frame and the distal frame including a portion for contacting the internal wall of a vessel to be occluded;
at least one occlusion membrane attached to the distal frame at a proximal end of the distal frame and to the proximal frame at a distal end of the proximal frame, the occlusion membrane having a proximal first portion and a distal first portion extending longitudinally for contacting the internal wall of the vessel to be occluded, and a proximal second portion distally adjoining the proximal first portion and a distal second portion proximally adjoining the distal first portion, the proximal and distal second portions directed away from the internal wall of the vessel and toward the longitudinal axis, the occlusion membrane being attached to the frame at least at the proximal and distal first portions, the at least one occlusion membrane radially surrounding at least the proximal end of the distal frame and the distal end of the proximal frame with the proximal and distal first portions, wherein expanding the device within a vessel causes the occlusion membrane to form a physical barrier within a vessel to be occluded, the occlusion membrane having an hourglass shape between the proximal end of the distal frame and the distal end of the proximal frame when expanded; and
a barrier located longitudinally between the distal end of the proximal frame and the proximal end of the distal frame, the barrier extending from the occlusion membrane across a lumen of the device and comprising a closable opening for receiving a guidewire, the barrier comprising a valve biased closed and arranged to not allow blood flow therethrough, the valve comprising leaves which are biased to a closed configuration, the barrier being deformed or relaxed to the closed configuration such that the leaves overlap to form a static screen across the lumen of the device upon removal of the guidewire.

2. The occlusion device of claim 1 wherein the occlusion membrane forms at least one substantially conical portion in the expanded state.

3. The occlusion device of claim 1 wherein the device is bidirectional and wherein the occlusion membrane forms two substantially conical portions in the expanded state.

4. The occlusion device of claim 1 wherein the occlusion membrane is graft material.

5. The occlusion device of claim 1 wherein the occlusion membrane is not fabricated from a bioabsorbable material.

6. The occlusion device of claim 1 wherein the barrier is made of silicone, polyurethane, expanded PTFE, a plastic material, or graft material.

7. The occlusion device of claim 1 wherein the occlusion membrane is attached to the frame internally.

8. The occlusion device of claim 1 wherein the frames are self-expanding.

* * * * *